United States Patent [19]

Quatrochi et al.

[11] Patent Number: 5,059,179
[45] Date of Patent: Oct. 22, 1991

[54] NON-REUSABLE SYRINGE ASSEMBLY

[76] Inventors: David Quatrochi, 7474 E. Arkansas, Ste. 2208, Denver, 80231; John K. Malone, 2955 Glenwood, No. 315, Boulder, Colo. 80301

[21] Appl. No.: 351,527
[22] Filed: May 15, 1989
[51] Int. Cl.$^5$ .............................................. A61M 5/00
[52] U.S. Cl. .................................. 604/110; 604/218; 604/228
[58] Field of Search .................. 604/110, 218–219, 604/224, 228–229, 233

[56] References Cited

U.S. PATENT DOCUMENTS

| 729,011 | 5/1903 | Tagliabue et al. | 604/219 |
| 2,688,325 | 9/1954 | Lockhart | 604/220 |
| 3,128,765 | 4/1964 | Tint | 604/228 X |
| 3,811,441 | 5/1974 | Sarnoff | 604/218 |
| 3,820,652 | 6/1974 | Thackston | 206/365 |
| 3,890,971 | 6/1975 | Leeson et al. | 128/218 R |
| 4,197,846 | 4/1980 | Bucalo | 128/218 P |
| 4,252,118 | 2/1981 | Richard et al. | 128/218 P |
| 4,367,738 | 1/1983 | Legendre et al. | 128/218 PA |
| 4,391,272 | 7/1983 | Staempfli | 604/110 |
| 4,493,703 | 1/1985 | Butterfield | 604/110 |
| 4,675,005 | 6/1987 | Deluccia | 604/110 |
| 4,685,910 | 8/1987 | Schweizer | 604/218 |
| 4,699,614 | 10/1987 | Glazier | 604/110 |
| 4,713,056 | 12/1987 | Butterfield | 604/110 |
| 4,731,068 | 3/1988 | Hesse | 604/110 |
| 4,781,684 | 11/1988 | Trenner | 604/110 |

FOREIGN PATENT DOCUMENTS 340314  9/1959  Switzerland .

Primary Examiner—C. Fred Rosenbaum
Assistant Examiner—Corrine Maglione
Attorney, Agent, or Firm—John E. Reilly

[57] ABSTRACT

A non-reusable syringe is made up of a hollow barrel with a hypodermic needle in communication with one end of the barrel, and a plunger assembly including a plunger movable in tight-fitting engagement through the interior of the barrel and a plunger shaft which extends axially away from the plunger and is releasably connected to one end of the plunger in such a way that relative rotation of the shaft with respect to the plunger in one direction will cause separation of the shaft from the plunger but reverse rotation will maintain the shaft and plunger in connected relation. A nut or keeper is positioned at the opposite end of the barrel to impart rotation to the shaft in response to axial movement of the shaft through the barrel.

8 Claims, 2 Drawing Sheets

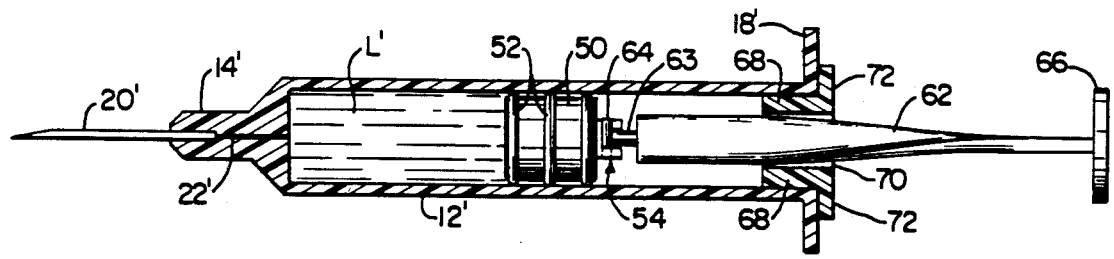
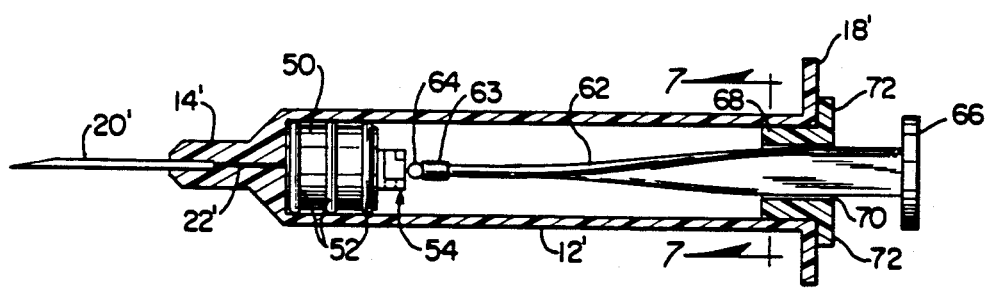
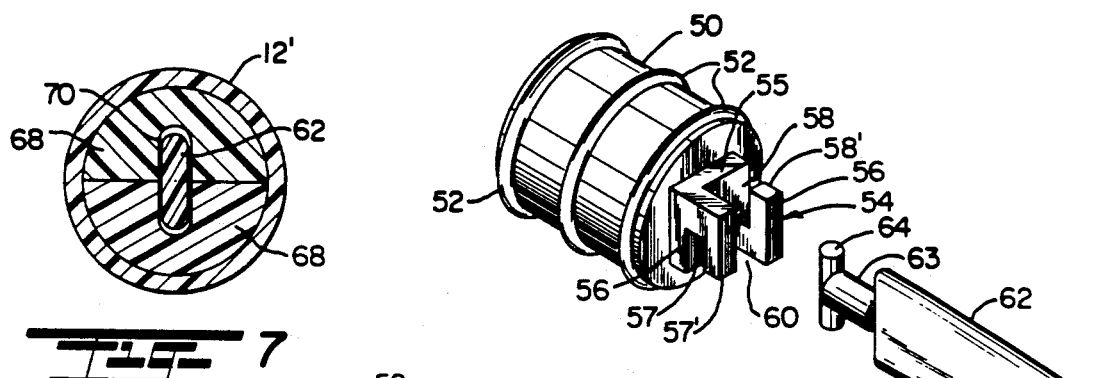
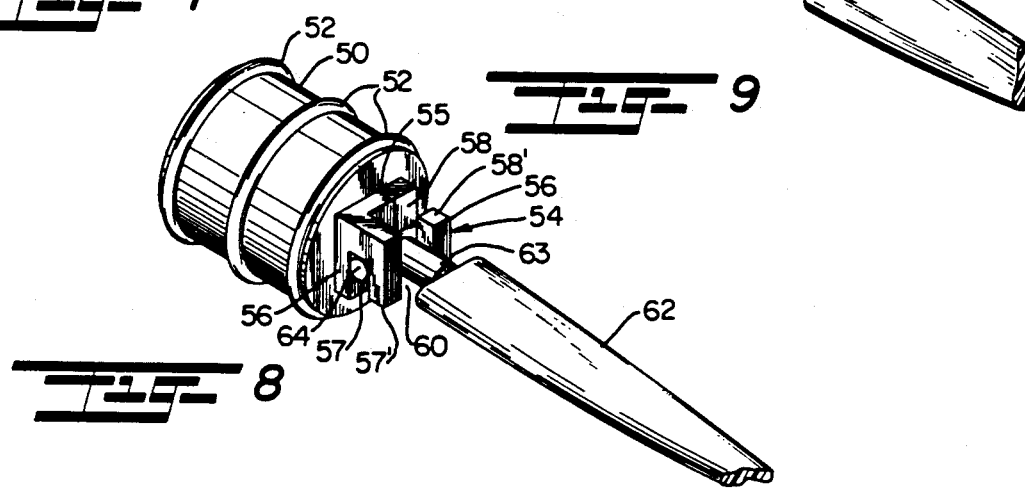

5,059,179

NON-REUSABLE SYRINGE ASSEMBLY

This invention relates to syringes; and more particularly relates to a novel and improved medical syringe which cannot be refilled after a single use.

BACKGROUND AND FIELD OF THE INVENTION

Numerous proposals have been made for avoiding communication of disease through sharing of hydrodermic needles or syringes. For instance, one of the leading causes of the spread of AIDS (Acquired Immune Deficiency Syndrome) is through intravenous injection of drugs through the use and reuse of needles by different persons. Furthermore, at medical institutions it is important to insure that an injection is not administered from a previously used syringe.

Previously, proposals have been made to construct a non-reusable syringe but none to the best of my knowledge has proven to be commercially acceptable or recognized for use by the medical profession. Among other problems in the past design of non-reusable syringes are the relatively high cost of construction and assembly, reliability in use and necessity of education of the user. Of the proposals made in the past, one approach has been to use a ratchet arrangement which will permit the plunger assembly to be advanced forwardly through the barrel of the syringe in forcing the material to be dispensed through a hypodermic needle at one end of the barrel but will not allow the plunger to be retracted or withdrawn through the barrel in order to refill the syringe. Representative of that approach are U.S. Pat. Nos. 4,731,068 to Hesse and 4,449,703 to Butterfield. Another approach taken in the past has been provision for the combination of a threaded plunger stem and a spiral complementary groove along the interior of a sleeve element which fits into the barrel of a syringe and representative of that approach is the Swiss Patent No. 340,314. However, this design is not capable of preventing reloading or reuse of the syringe. Other representative patents in this field are U.S. Pat. Nos. 3,820,652 to Thackston and 4,781,684 to Trenner.

SUMMARY OF THE INVENTION

Accordingly, it is an object of the present invention to provide for a novel and improved syringe assembly that is rendered useless and cannot be reloaded after a single use.

It is another object of the present invention to prevent the spread of communicable diseases through the sharing of hypodermic needles by different persons and in general to assure that an injection cannot be administered from a previously used syringe.

It is a further object of the present invention to provide for a novel and improved syringe assembly of simplified construction that is inexpensive to fabricate and assemble and is dependable in use.

A still further object of the present invention is to provide for a novel and improved syringe assembly which is comprised of a minimum number of parts and requires a minimum of instructions for proper use.

In accordance with the present invention, there has been devised a novel and improved syringe of the type having an elongated generally cylindrical barrel with a hypodermic needle in communication with one end of the barrel, the improvement comprising a plunger sized for movement in tightfitting engagement with the interior of the barrel between the one end and an opposite end of the barrel, a plunger shaft extending axially of the barrel including means releasably connecting the shaft to the plunger whereby relative rotation of the shaft with respect to the plunger in one direction will cause separation of the shaft from the plunger, and means at the opposite end of the barrel for imparting rotation to the shaft in response to axial movement of the shaft through the barrel. An important feature of the invention is to prevent rotational movement of the plunger as the plunger shaft is moved in the direction of withdrawal through the barrel so that independent rotation of the plunger shaft will cause its immediate separation from the plunger after it has advanced the plunger axially through the barrel to discharge the contents therefrom.

The above and other objects, advantages and features of the present invention will become more readily appreciated and understood from a consideration of the following detailed description of a preferred embodiment of the present invention when taken together with the accompanying drawings of preferred embodiments of the present invention, in which:

BRIEF DESCRIPTION OF THE DRAWINGS

FIG. 5 is another view partially in section of the syringe shown in FIG. 4 with the plunger partially retracted through the barrel in drawing liquid into the barrel;

FIG. 6 is a sectional view of the form of invention shown in FIGS. 4 and 5 and illustrating the separation between the plunger shaft and plunger when the plunger is advanced to its forwardmost position to discharge the fluid contents in the barrel;

FIG. 7 is a cross-sectional view taken about lines 7—7 of FIG. 6;

FIG. 8 is a somewhat fragmentary perspective view of the plunger shaft and plunger in connected relation as further illustrated in FIGS. 4 and 5; and FIG. 9 is another somewhat fragmentary perspective view illustrating the separation between the plunger shaft and plunger as shown in FIG. 6.

DETAILED DESCRIPTION OF THE PREFERRED EMBODIMENT

Figure 1:
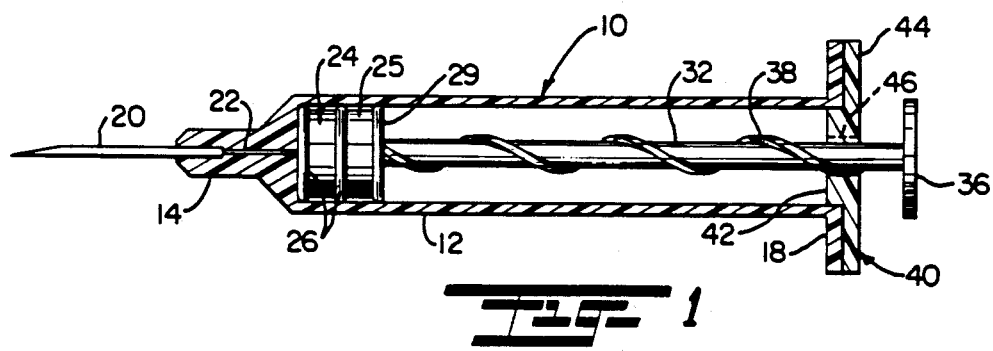
FIG. 1 is a view partially in section of a first preferred embodiment of the syringe in accordance with the present invention and illustrating the plunger in an advanced position with respect to the barrel.
Figure 2:
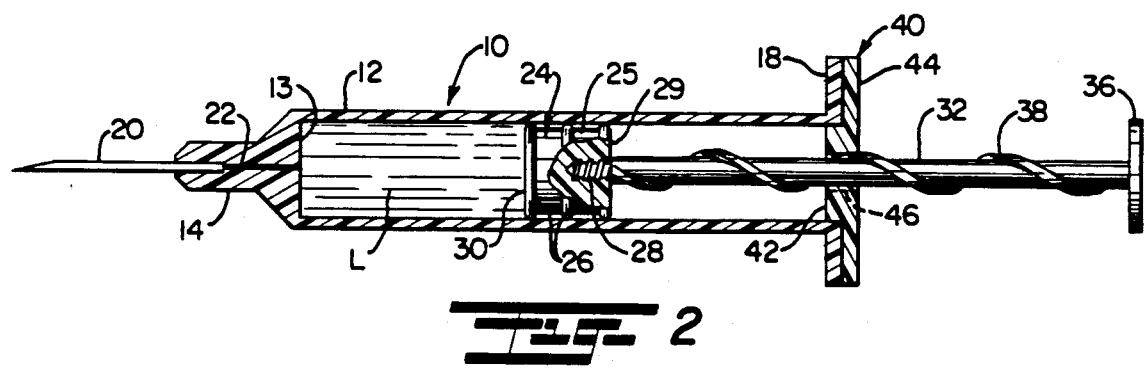
FIG. 2 is another view partially in section of the form of invention illustrated in FIG. 1 but with the plunger partially retracted through the barrel in drawing liquid into the barrel.
Figure 3:
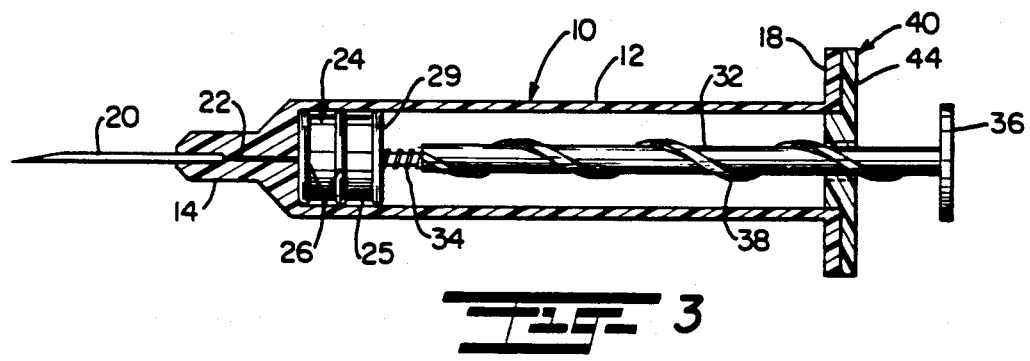
FIG. 3 is a view partially in section of the syringe of FIGS. 1 and 2 and illustrating separation of the plunger shaft from the plunger in the advanced position to discharge the fluid contents in the barrel.

Referring in detail to the drawings, there is illustrated in FIGS. 1 to 3 a first preferred form of syringe assembly 10 which is comprised of an elongated, generally cylindrical barrel 12. The barrel 12 has a hollow interior which is of uniform diameter throughout, and the wall of the barrel converges at its forward end into a hub 14. The opposite end of the barrel has an external flange or finger grip 18 to facilitate grasping of the assembly. A hypodermic needle 20 is inserted into the hub 14 and in sealed engagement therewith to communicate with a bore 22 which extends through the hub into communication with the hollow interior of the barrel 12.

A plunger assembly includes a plunger 24 disposed in the hollow interior of the barrel 12 for axial movement therethrough, the plunger comprising a short, solid cylindrical body 25 provided with external, circumferentially extending ribs 26 at spaced intervals along the plunger. Preferably, the plunger is composed of a rubber or rubber-like material and is sized such that the ribs 26 will frictionally engage the inner wall surface of the barrel and establish close-fitting sealed engagement therewith. A female end in the form of a threaded bore 28 extends axially through one end 29 of the plunger for a limited distance, and the opposite end 30 of the plunger is substantially flat and capable of movement into flush engagement with end wall surface 13 of the barrel adjacent to the hub. A second part of the plunger assembly is defined by a plunger shaft 32 of substantially reduced diameter with respect to the plunger and has a male end in the form of a threaded extension 34 at its leading end which is complementary to the threading of the bore 28 in the plunger so that the plunger shaft can be threadedly connected to the plunger and extend rearwardly away from the plunger centrally of the interior of the barrel. The shaft 32 is dimensioned to be of a length to extend beyond the flanged end portion 18 of the barrel and is provided with a finger grip 36 at its exposed or external end. A spiral rib 38 is formed on the external surface of the plunger shaft 32, the rib 38 being of opposite hand to that of the threading 28 and extends along the substantial length of the shaft.

A nut 40 is assembled onto the opposite end of the barrel 12 to that of the hub 14, the nut having a thickened cylindrical portion 42 which is sized for insertion into close-fitting relation to the inner wall surface of the barrel 12 and an external shoulder or enlarged head 44 which is superimposed on the flanged end portion 18. Preferably, the nut is composed of a plastic material which can be permanently affixed to the end of the barrel 12 by a bonding agent or by sonically welding the elements together so that the nut 40 effectively closes the top end of the barrel. A threaded bore 46 extends centrally of the nut with an internal spiral groove to threadedly engage the spiral rib 38.

The elements comprising the syringe assembly 10 are assembled together in the following manner: The plunger 24 is threaded onto the end of the plunger shaft 32 and inserted into the barrel 12 until it reaches the position illustrated in FIG. 1 abutting the end 13 of the barrel. The nut 40 is loosely assembled onto the plunger shaft 32 as a preliminary to the initial insertion of the plunger 24 into the barrel. Once in the positional relationship shown in FIG. 1, the nut is inserted into the flanged end portion 18 of the barrel and permanently attached as described so that any further movement of the plunger shaft 32 is solely by rotation through the nut 40. In order to load the barrel, the plunger shaft 32 is axially advanced in a direction withdrawing the plunger from the leading end of the barrel so as to create a vacuum tending to induce the flow of liquid to be dispensed into the barrel chamber or interior, the liquid being generally designated at L in FIG. 2. It will be noted that, as the plunger shaft is retracted and is caused to rotate through the nut 40, its direction of rotation is such that the extension 34 will rotate in a direction tending to tighten it with respect to the threaded bore 28. Accordingly, while the plunger 24 will resist rotation as it is being axially withdrawn by the plunger shaft, it will nevertheless be forced to rotate with the shaft by virtue of the direction of rotation of the shaft with respect to the plunger 24. When the liquid contents are to be discharged from the barrel, the plunger shaft 32 is advanced forwardly as illustrated in FIG. 3 until the plunger 24 reaches the end 13 of the barrel; and as the plunger shaft 32 is advanced through the nut and caused to rotate in a clockwise direction will impart rotation to the extension 34 in a direction causing it to be unthreaded or released from the plunger 24, since again the plunger 24 is restrained against rotation by virtue of its frictional engagement with the inner wall surface of the barrel 12. As a result, by the time the plunger reaches the leading end 13 of the barrel, the extension 34 will have become separated or disengaged from the plunger so that the plunger will remain in the leading end of the barrel. In other words, if the plunger shaft is once again withdrawn through the barrel, the plunger will not follow its movement and it will not be possible to refill the barrel.

DETAILED DESCRIPTION OF SECOND PREFERRED EMBODIMENT

There is illustrated in FIGS. 4 to 8 another preferred embodiment of the present invention wherein like parts to those of FIGS. 1 to 3 are correspondingly enumerated. Briefly, barrel 12' has a hub 14' into which needle 20' is inserted for communication with the interior of the barrel through a bore 22'. The opposite end of the barrel 12' similarly has a flanged end portion 18'. A modified form of plunger assembly comprises a plunger body 50 having external ribs 52 which extend circumferentially of the body at axially spaced intervals. The plunger 50 is sized such that the ribs 52 establish close-fitting engagement with the inner wall surface of the barrel 12' and once again is composed of a rubber or rubber-like material which will frictionally engage the inner wall surface of the barrel to retard rotation. One end of the plunger 50 is provided with a square connecting end portion 54 having opposite sides 55 and 56. The sides 56 are provided with slotted portions 57 and 58 which open in opposite directions to one another, and a common open channel 60 extends between the sides 56 and is in communication with the slotted portions 57 and 58.

Figure 4:
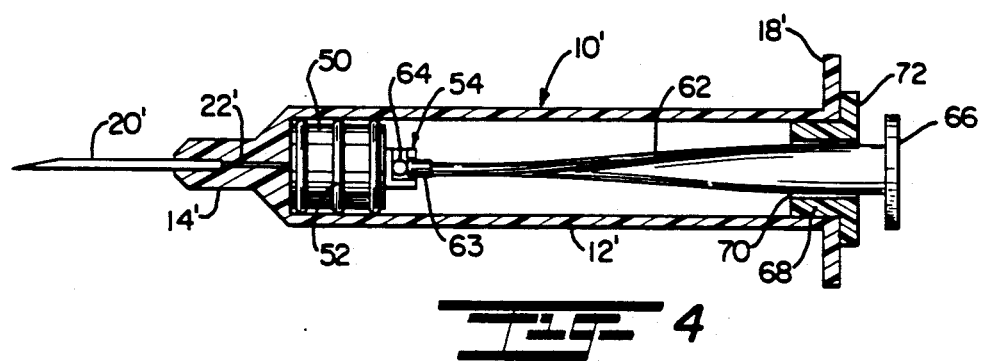
FIG. 4 is a view partially in section of another preferred embodiment of the syringe in accordance with the present invention and illustrating the plunger in an advanced position.

A plunger stem or shaft 62 is of a generally oval-shaped cross-sectional configuration and twisted or convoluted at 90°; i.e., the major axes at opposite ends of the stem are at 90° to one another. The leading end of the stem 62 is provided with an axially extending rod 63 and to which is affixed a transversely extending pin 64, and oppositely directed ends of the pin 64 are insertable into the slots 57 and 58 of the block 55. The opposite end of the shaft 62 terminates in a handle grip 66. Semicircular keepers or ring members 68 are assembled onto the end of the inner wall surface at the opposite end of the barrel and together form an oblong slot or guide 70 therebetween through which the plunger shaft 62 extends. Each of the keepers is provided with external shoulders or extensions 72 which overlie the flanged end portion 18' when the keepers 68 are inserted into the barrel 12'. The keepers are affixed to the flanged end of the barrel 12' once the plunger assembly has been fully inserted with the plunger 50 engaging the leading of the barrel, as illustrated in FIG. 4, and the shaft 62 has its pin member 64 fully inserted into the slots 57 on the end portion 54. When the plunger shaft 62 is withdrawn through the keepers, it will cause the pin 64 to be rotated in a clockwise direction so as to maintain its locked or engaged position with respect to the closed ends of the slots 57 in drawing liquid or serum L' into the interior of the barrel, for example, in moving to the position shown in FIG. 5. However, when the plunger shaft 62 is advanced forwardly, its engagement with the keepers 68 will cause it to be rotated in a counterclockwise direction thereby rotating the pin 64 in a direction away from the closed ends of the slot 57, or in other words, will move into a position in which the pin 64 is parallel to the channel 60 and completely out of engagement with the slots 57. Specifically, this will occur in the course of advancement of the plunger 50 from a position such as that shown in FIG. 5 to that shown in FIG. 6 in the course of discharging the liquid L' through the needle 20'. As further illustrated in FIG. 6, if the shaft 62 is reversed in movement and caused to rotate in the opposite direction of withdrawal from the barrel 12', the pin 64 will have moved axially away from engagement with the channel 60 before it has an opportunity to rotate into engagement with the slots 57 so that the plunger 50 will remain in the bottom of the barrel 12' and prevent reloading of the syringe.

The twisted, oval-shaped shaft 62 of the second preferred form shown in FIGS. 4 to 8 will undergo more gradual rotation in relation to axial movement than the shaft 32 of FIGS. 1 to 3 in order to insure that the pin 64 will not reengage the slots 57 when the shaft is retracted through the barrel. Nevertheless, it will be evident that a shaft 32 of the type illustrated in FIGS. 1 to 3 may be employed in combination with the releasable connecting means of the form shown in FIGS. 4 to 8; namely, the pin 64 and slotted block 54 in place of the threaded connection 28 and 34 of the form of FIGS. 1 to 3. Moreover, the effective length of the slots 57 can be adjusted specifically by shortening the legs 57' to assure that the pin 64 will not accidentally reengage the slots after the initial use of the syringe.

Although the slotted end portion 54 has been illustrated as being of generally square or rectangular configuration, it will be evident that it may be of rounded or generally circular configuration so that the slotted portions 57 and legs 57' are arcuate and in diametrically opposed relation to one another. The relative pitch established between the spiral ribbing 38 on the shaft 32 to that of the threaded end 34 may be varied according to the length of the barrel and amount of liquid to be drawn into the barrel and discharged therefrom. The most important criterion is the amount of rotation needed to effectively separate the threaded end 34 from the bore 28 when the plunger is advanced into the position shown in FIG. 3 in order to assure complete separation between the parts if any attempt is made to reuse the assembly.

The parts comprising the forms of invention as described may be composed entirely of disposable plastic materials and very inexpensively manufactured and produced. As described, a minimum number of steps is required in the assembly. Also, it will be appreciated that a standard barrel and cannula may be used in combination with either type of plunger assembly shown in FIGS. 1 to 3 or 4 to 8.

It is therefore to be understood that the foregoing and other modifications and changes may be made in the construction and arrangement of parts comprising the forms of invention illustrated and described without departing from the spirit and scope of the present invention as defined by the appended claims and reasonable equivalents thereof.

I claim:

1. In a syringe having an elongated, generally cylindrical barrel with a hollow interior and a hypodermic needle at one end of said barrel in sealed communication through an opening with the hollow interior of said barrel, the improvement comprising:
   a plunger sized for disposition in tight-fitting engagement with the interior of said barrel for axial movement between said one end and an opposite end thereof;
   a plunger shaft extending axially through the interior of said barrel including means releasably connecting said shaft to said plunger whereby relative rotation of said shaft with respect to said plunger in one direction will cause disconnection of said shaft from said plunger, said releasable connecting means defined by male and female complementary threaded end portions between said plunger and said shaft; and
   means permanently affixed to said opposite end of said barrel for imparting rotation to said shaft in response to axial movement of said shaft through said barrel.

2. In a syringe according to claim 1, said rotation-imparting means including complementary threaded portions between said shaft and said opposite end of said barrel.

3. In a syringe according to claim 2, said rotation-imparting means having a threaded portion of opposite hand to said releasable connecting means and including a nut member permanently affixed to said opposite end of said barrel whereby axial movement of said shaft toward the one end of said barrel will cause disconnection of said shaft from said plunger.

4. In a syringe according to claim 3, said rotation-imparting means having said threaded portions of a pitch less than the pitch of said threaded end portions of said releasable connecting means.

5. In a syringe according to claim 1, said releasable connecting means including a threaded end portion on said shaft and a threaded bore at one end of said plunger defining said male and female threaded end portions, respectively.

6. A medical syringe comprising in combination an elongated, generally cylindrical barrel provided with a hollow interior and a hypodermic needle at one end of said barrel in sealed communication through an opening with the hollow interior of said barrel:
   a plunger disposed in tight-fitting engagement with said interior of said barrel for axial movement between said one end and an opposite end thereof;
   a plunger shaft extending axially through the interior of said barrel including means releasably connecting said shaft to one end of said plunger whereby relative rotation of said shaft with respect to said plunger in one direction will cause separation of said shaft from said plunger, said releasable connecting means including a block at one end of said plunger provided with slotted portions on diametrically opposed sides of said shaft, and a cross pin extending transversely of said plunger shaft and disposed at the leading end of said plunger shaft being rotatable into and out of engagement with said slotted portions, said slotted portions extending in a direction aligned with the rotational movement of said crosspin; and means at said opposite end of said barrel for imparting rotation to said shaft in response to axial movement of said shaft through said barrel.

7. In a syringe having an elongated, generally cylindrical barrel with a hollow interior and a hypodermic needle at one end of said barrel in sealed communication through an opening with the hollow interior of said barrel, the improvement comprising:

a plunger sized for disposition in tight-fitting engagement with the interior of said barrel for axial movement between said one end and an opposite end thereof;

a plunger shaft extending axially through the interior of said barrel including means releasably connecting said shaft to said plunger whereby relative rotation of said shaft with respect to said plunger in one direction will cause disconnection of said shaft from said plunger, said shaft being of generally oval-shaped configuration and convoluted along its length and having a major axis at one end disposed at 90° to the major axis at the opposite end thereof; and means for imparting rotation to said shaft in response to axial movement of said shaft through said barrel.

8. A medical syringe comprising in combination:

an elongated, generally cylindrical barrel provided with a hollow interior and a hypodermic needle at one end of said barrel in sealed communication through an opening with the hollow interior of said barrel:

a plunger disposed in tight-fitting engagement with said interior of said barrel for axial movement between said one end and an opposite end thereof;

a plunger shaft extending axially through the interior of said barrel including means releasably connecting said shaft to one end of said plunger whereby rotation of said shaft with respect to said plunger in one direction will disconnect said shaft from said plunger, said releasable connecting means including a block at one end of said plunger provided with slotted portions on diametrically opposed sides of said shaft, and a cross pin extending transversely of said plunger shaft and disposed at the leading end of said plunger shaft being rotatable into and out of engagement with said slotted portions, said slotted portions extending in a direction aligned with the rotational movement of said cross pin; and means at said opposite end of said barrel for imparting rotation to said shaft in the one direction in response to axial movement of said shaft toward said one end of said barrel whereby to disconnect said shaft from said plunger, said shaft being of generally oval-shaped configuration and convoluted along its length, said shaft having a major axis at one end disposed at 90° to the major axis at the opposite end thereof.

* * * * *